United States Patent [19]

Feist et al.

[11] Patent Number: 4,592,708

[45] Date of Patent: Jun. 3, 1986

[54] APPARATUS FOR MAKING AIRLAID ARTICLES

[75] Inventors: Barry R. Feist, Cincinnati; Jerry E. Carstens, Mason; David A. Peterson, Cincinnati, all of Ohio

[73] Assignee: The Procter & Gamble Company, Cincinnati, Ohio

[21] Appl. No.: 576,098

[22] Filed: Feb. 1, 1984

[51] Int. Cl.[4] .............................................. B27N 3/14
[52] U.S. Cl. ..................................... 425/80.1; 19/148; 264/517; 264/121
[58] Field of Search ..................... 425/80.1, 81.1, 83.1; 264/37, 112, 113, 121, 503, 517, 518, DIG. 75; 19/148, 303; 156/62.2

[56] References Cited

U.S. PATENT DOCUMENTS

| | | | |
|---|---|---|---|
| 2,073,329 | 3/1937 | Winter | 154/33 |
| 2,218,338 | 10/1940 | Manning | 264/DIG. 75 |
| 2,940,133 | 6/1960 | Heritage | 264/518 |
| 3,235,913 | 2/1966 | Schuller | 156/62.2 |
| 3,518,726 | 7/1970 | Banks | 19/144.5 |
| 3,772,739 | 11/1973 | Lovgren | 425/81.1 |
| 3,900,921 | 8/1975 | Zafiroglu | 264/518 |
| 4,005,957 | 2/1977 | Savich | 425/80 |
| 4,264,289 | 4/1981 | Day | 425/83.1 |
| 4,375,447 | 3/1983 | Chung | 264/518 |
| 4,382,758 | 5/1983 | Nopper et al. | 425/83.1 |

Primary Examiner—Jay H. Woo
Assistant Examiner—J. Fortenberry
Attorney, Agent, or Firm—Thomas J. Slone; Fredrick H. Braun; Richard C. Witte

[57] ABSTRACT

An apparatus for making airlaid articles such as discrete absorbent cores for catamenial napkins and disposable diapers and the like. Apparatus embodying the invention preferably comprises a laydown drum having a plurality of formation cavities having foraminous bottom walls, which cavities are circumferentially spaced around the perimeter of the drum. The apparatus also preferably includes means for directing a high velocity stream of air-entrained matter such as, for example, fibers or particulate matter, substantially radially towards a relatively short circumferential span of the perimeter of the drum; and a hood having sufficient circumferential span of the drum to enable excess entrainment air to be drawn by vacuum through the foraminous bottom walls of substantially empty cavities, and to enable recirculation of the excess scarfed fibers. The method preferably includes overfilling the cavities; scarfing and recycling the excess; and compacting the deposited mass of fibers to impart structural integrity to the mass of fibers to dimensionally define the articles prior to removing the articles from their respective formation cavities.

18 Claims, 3 Drawing Figures

APPARATUS FOR MAKING AIRLAID ARTICLES

DESCRIPTION

1. Technical Field

This invention pertains to forming airlaid articles such as discrete absorbent cores for catamenial napkins or disposable diapers. More particularly it pertains to forming such discrete articles having irregular shapes—particularly non-uniform thicknesses—on a drum-type deposition apparatus.

2. Background Art

A drum-type airlaying apparatus for making discrete absorbent fibrous articles is disclosed, for example, in U.S. Pat. No. 2,073,329 which issued Mar. 9, 1937 to C. P. Winter, and which includes a broadly divergent duct which extends from his drylap disintegrator (i.e., means for air entraining fibers) to the periphery of his first deposition drum. Another drum-type airlaying apparatus for airlaying discrete absorbent fibrous articles which has a similarly broadly divergent duct for air-entrained fiber flow is disclosed in U.S. Pat. No. 4,005,957 which issued Feb. 1, 1977 to Peter P. Savich. A drum-type airlaying apparatus for making a concatinated stream of absorbent fibrous articles is disclosed in U.S. Pat. No. 3,518,726 which issued July 7, 1970 to C. T. Banks. A belt-type airlaying apparatus having a duct for air-entrained fibers which is sharply angled obliquely downstream with respect to the laydown belt is disclosed in U.S. Pat. No. 4,375,447 which issued Mar. 1, 1983 to Raymond Chung. As compared to the present invention, these are representative patents which disclose airlaying apparatus wherein the ducts for directing and confining air-entrained fibers flowing towards their respective foraminous deposition surfaces or cavities effect deposition of fibers on the entire lengths of their deposition surfaces traversing the machine direction spans of their ducts. Thus, essentially, the entrainment air which carries fibers onto their deposition surfaces is drawn by vacuum means through the portions of the foraminous deposition surfaces disposed subjacent their respective deposition sites rather than having the bulk of the entrainment air drawn through remotely disposed portions of the deposition surfaces which are relatively free of airlaid fibers as is provided by the present invention.

DISCLOSURE OF THE INVENTION

In accordance with one aspect of the invention, an improved drum-type airlaying apparatus for making discrete absorbent fibrous articles of airlaid matter such as fibers or other particulate matter is disclosed. The apparatus is of the type which includes a rotating deposition drum having a plurality of article formation cavities disposed in circumferentially spaced relation about the periphery of the deposition drum and wherein each of the cavities has a foraminous bottom wall; means for directing air-entrained fibers towards the periphery of the drum; and means for vacuum drawing the entrainment air through the foraminous bottom walls of the cavities and exhausting it from the apparatus. The improvement provides that the means for directing air-entrained fibers comprises means for directing a stream—preferably a substantially columnar stream or jet—of air-entrained fibers substantially radially towards and against a predetermined first sector of the periphery of the drum; and that the means for vacuum drawing the entrainment air through the foraminous bottom walls of the cavities comprises means for the entrainment air to be drawn through the foraminous bottom wall of at least one substantially empty cavity disposed in a predetermined second sector of the drum disposed upstream from the first sector. The apparatus may further comprise means for imparting a sufficient downstream velocity vector component to the air-entrained fibers to offset the effect of the circumferential velocity of the drum; means for maintaining sub-ambient pressure adjacent the first sector of the drum; means for controlling the velocity of the air-entrained stream at predetermined value in preferred velocity ranges; means for controlling the air to fiber weight ratio in the air-entrained stream; means for adjusting the air-flow-direction length of the radially directed stream of air-entrained fibers; means for controlling the rate of airflow of the stream of air-entrained fibers; means for overfilling each cavity, and scarfing and recycling the excess; and means for compacting each discrete absorbent fibrous article prior to its being removed from its respective formation cavity. The apparatus may additionally comprise means disposed adjacent the drum for effecting additional compaction of the articles after they are forwarded from the drum which means may comprise a pair of linear conveyors disposed in opposed relation and convergent in the downstream direction; and calendering means for effecting additional overall or contoured compaction. The method of the present invention provides, essentially, high velocity injection of fibers into a cavity to effect formation of a discrete absorbent fibrous article, and exhausting the entrainment air through substantially empty additional cavities disposed upstream from the cavity into which the fibers are being injected and deposited.

BRIEF DESCRIPTIONS OF THE DRAWINGS

While the specification concludes with claims which particularly point out and distinctly claim the subject matter regarded as forming the present invention, it is believed the invention will be better understood from the following descriptions taken in conjunction with the accompanying drawings in which identical features in the several views are identically designated and in which:

DETAILED DESCRIPTION OF THE INVENTION

Figure 1:
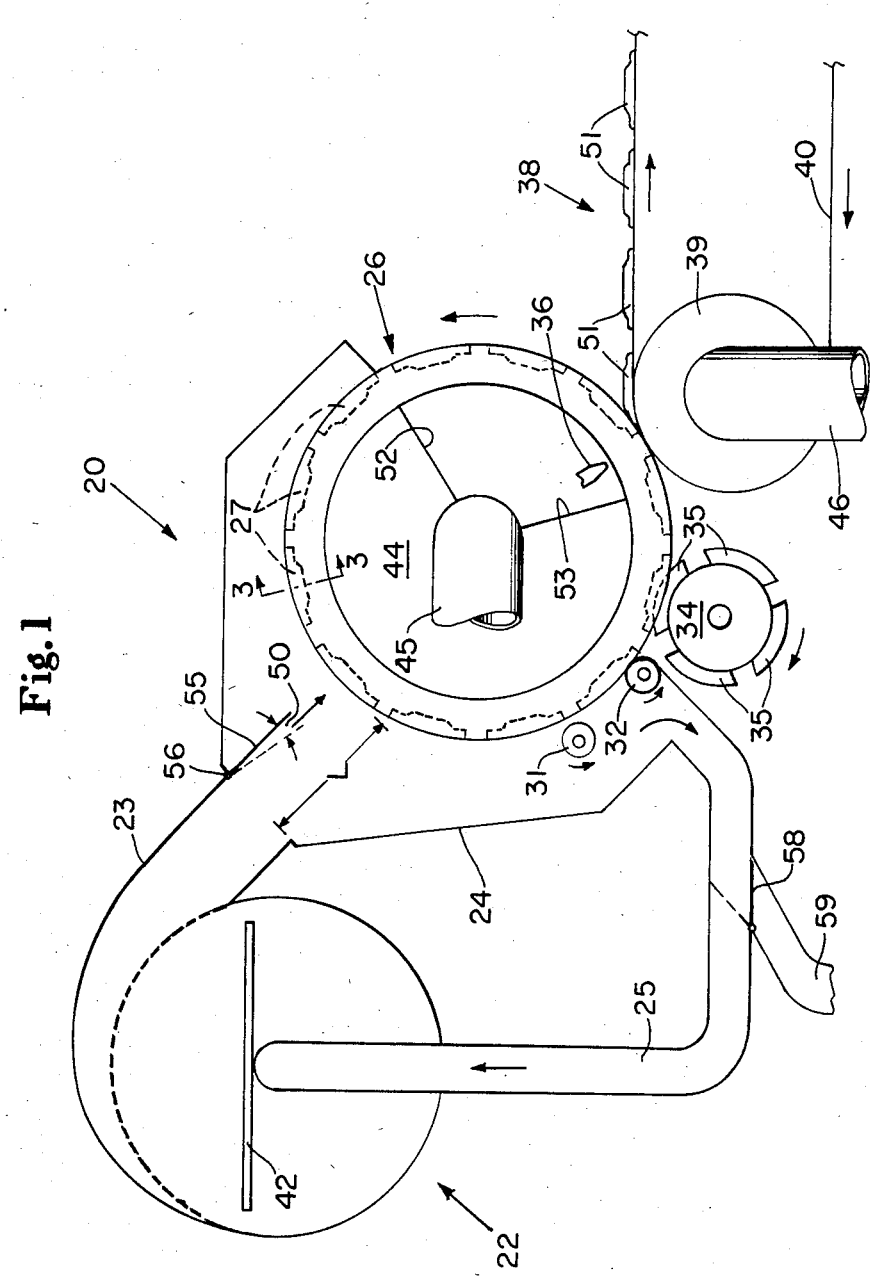
FIG. 1 is a somewhat schematic, fragmentary side elevational view of an apparatus embodiment of the present invention.

A fragmentary portion of an exemplary drum-type apparatus for making discrete absorbent fibrous articles such as cores of catamenial napkins or disposable diapers in accordance with the present invention is designated 20 in FIG. 1. As further shown in FIG. 1, apparatus 20 comprises a disc-type hammermill 22 having a columnar discharge chute 23, a hood 24, a recirculation manifold 25, a deposition drum 26 having a plurality of deposition cavities 27 disposed in circumferentially spaced relation about its periphery, two scarfing rolls 31 and 32, a lugged cylinder 34 having a plurality of radially extending lugs 35, a blow-off means or nozzle 36 and a take-away conveyor 38 comprising a vacuum-type return roll 39 and a foraminous endless belt 40. Means not shown are provided for feeding a drylap web into infeed slot 42 of hammermill 22 at a predetermined rate; means for powering and controlling hammermill 22; means for rotating drum 26, scarfing rolls 31 and 32, and conveyor 38 in timed relation; means for maintaining a predetermined degree of vacuum in vacuum manifold 44 of drum 26 via vacuum duct 45, and means for maintaining a predetermined level of vacuum inside a sector of return roll 39 through vacuum duct 46. Additionally, a somewhat columnar stream 50 of air-entrained fibers is shown in FIG. 1 to be exiting from the discharge chute 23 of hammermill 22 and directed generally radially towards a sector of drum 26 having a relatively small circumferential length; and an endless stream of discrete absorbent fibrous articles 51 is shown moving rightwardly on belt 40 of take-away conveyor 38. As used herein, a drylap web is a web of fibers which are subject to being disassociated and air-entrained by the action, for example, of hammermill 22.

Briefly, apparatus 20 comprises means for converting an endless length or roll of drylap web into a stream of discrete absorbent fibrous articles having good edge definition and structural integrity. The hammermill—alternately designated a fiberizer or disintegrator—disassociates the fibers of the drylap web and then discharges a relatively high velocity stream of air-entrained fibers which stream is directed generally radially towards a relatively short circumferential span of the periphery of drum 26. The velocity and mass derived momentum of the fibers in the stream injects them into a deposition cavity disposed on the periphery of the drum while the substantially smaller momentum of the entrainment air enables the bulk of the entrainment air to turn upstream with respect to the periphery of the drum and be drawn through the foraminous bottom walls of substantially empty additional deposition cavities by the vacuum maintained in vacuum manifold 44 of drum 26. Indeed, as is more fully described hereinafter, each deposition cavity is preferably overfilled in its entirety (i.e., its full width and circumferential length), and the excess is scarfed away by scarfing rolls 31 and 32. Then, the masses of fibers disposed in each filled deposition cavity is compacted a predetermined amount by the action of a lug 35 on the lugged cylinder 34 to complete the formation of a discrete airlaid article 51 having good edge definition and structural integrity as a result of being compacted before being removed from its deposition cavity. This also reduces the degree of length/width growth of the articles if they are subjected to calendering after being removed from their formation cavities. The discrete articles are then transferred to the take-away conveyor by the joint action of the blow-off nozzle 36, and vacuum in a facing sector of the conveyor return roll 39. Parenthetically, the bulk of the entrainment air exits via substantially empty deposition cavities because of the flow impeding effect of the fiber build up in the deposition cavity passing under the stream 50 of air-entrained fibers.

Figure 2:
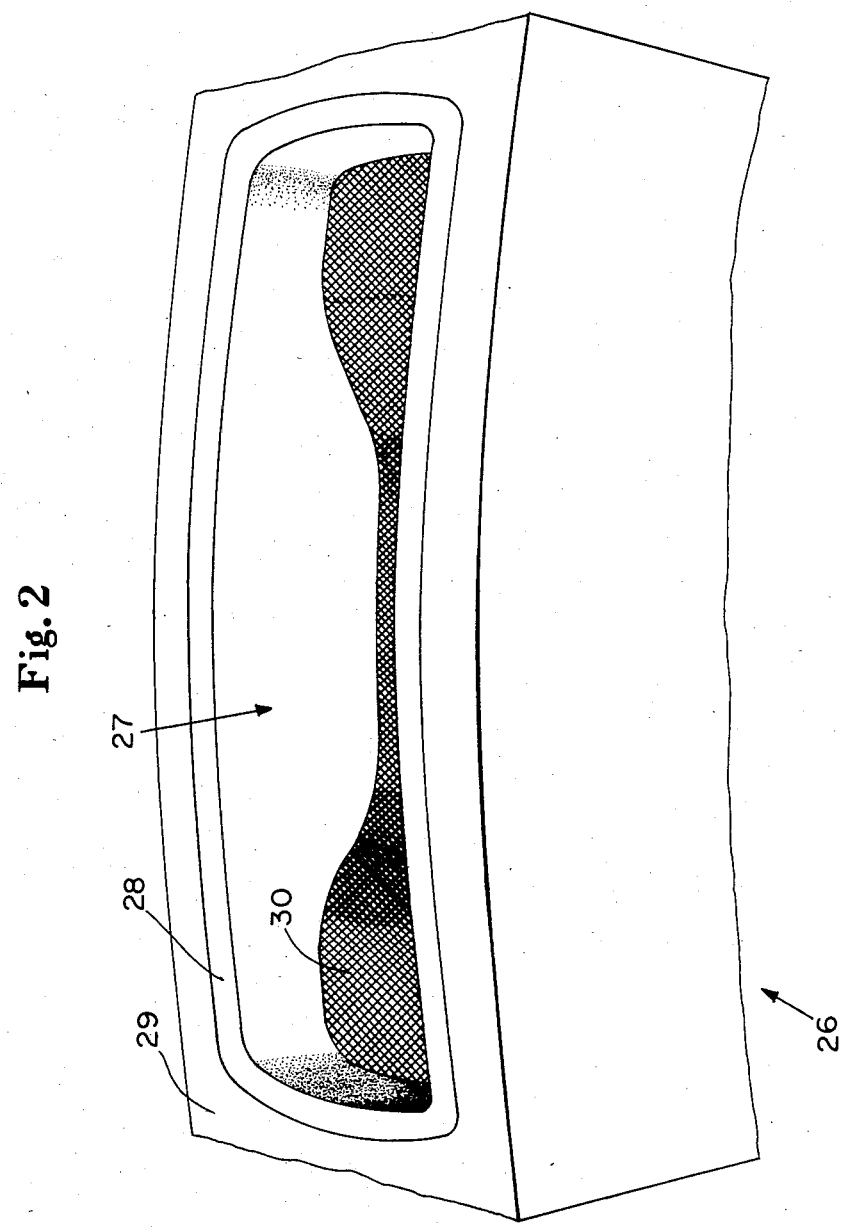
FIG. 2 is an enlarged scale, fragmentary perspective view of a deposition cavity disposed on the periphery of the deposition drum of the apparatus shown in FIG. 1.

A deposition cavity 27 is shown in a perspective view, FIG. 2, of a fragmentary portion of the periphery of deposition drum 26. The deposition cavity has a stepped configuration to provide articles 51 having substantially less basis weight (i.e., weight of fibers per unit of its plan-view area) in their end regions than their center spans. That is, as the articles 51 are formed they have generally uniform density, thick center spans and relatively thin end regions due to the geometry of the deposition cavities 27. Then, through the action of the lugged cylinder 34, the articles are compacted to achieve improved structural integrity, and to have their edges more clearly defined: i.e., the edges of the articles being made in the image of the edges of their formation cavities. This compaction also reduces the degree of length/width growth of the articles if they are subjected to further compaction or calendering after being removed from the deposition cavities as stated above. Preferably, the discrete articles 51 are calendered and enveloped in suitable covering materials and such other converting operations as desired are effected downstream from the deposition drum to produce finished disposable consumer products comprising airlaid fibrous cores; for example, catamenial napkins and/or disposable diapers.

Figure 3:
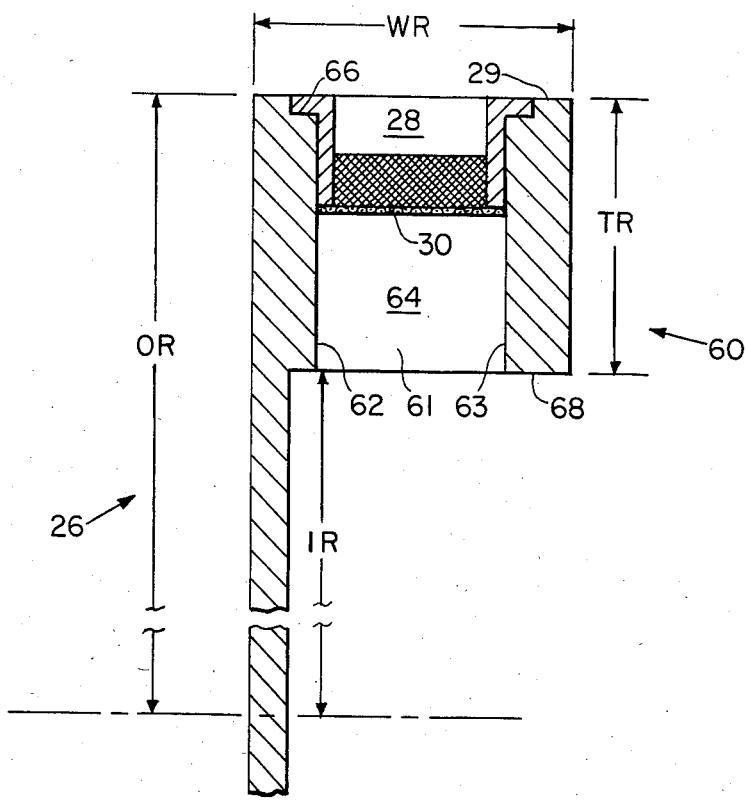
FIG. 3 is an enlarged scale, fragmentary sectional view taken along section line 3—3 of FIG. 1 which section line extends radially through the center of a deposition cavity disposed in the rim of the deposition drum of the apparatus shown in FIG. 1.

Referring now to FIG. 3, a transverse-radial section of drum 26 is shown to have an outer radius OR and inner radius IR; a rim 60 having a radial thickness TR and a transverse width WR. The rim 60 as shown in FIG. 3 has a radially extending hole 61 machined through it which hole, as shown is defined by side walls 62 and 63, and end walls 64, only one of the end walls being visible in the sectional view. Of course, hole 61 is only one of a plurality of such holes which are disposed in the rim of drum 26; one for each deposition cavity 27, FIG. 1, which in the exemplary apparatus 20 number twelve which are spaced at thirty degrees center-to-center. The radially outwardly facing surface of the rim has a recess 66 machined in it to accommodate the flange of a deposition cavity insert 28 so that the radially outwardly facing surface of the insert is flush with the radially outwardly facing surface of the rim, and so that together they constitute the periphery 29 of the drum. A piece of screen or otherwise foraminous material is secured to the bottom end of insert 28 to constitute its bottom wall 30. The surface of the drum having a radius IR is designated sealing surface 68. The vacuum manifold 44, FIG. 1, which is stationary (i.e., does not rotate with drum 26) is provided with sealing means which coact with sealing surface 68, FIG. 3, to enable the vacuum applied to the manifold to draw entrainment air downwardly through the cavities 27 and holes 61 which pass over the vacuum manifold as the drum rotates.

Referring again to FIG. 1, apparatus 20 is shown to further comprise an optional baffle plate 55 which is pivotally mounted on the upstream lip of chute 23 by pivot pin 56; a recirculation dump valve 58; and a recirculation dump duct 59. The angular position of baffle plate 55 can be adjusted to precipitate a downstream velocity vector component to the stream 50 of fibers to match the peripheral velocity of drum 26, or to otherwise provide a sufficient downstream velocity vector component of stream 50 to achieve even filling of both ends of the deposition cavities 27. The recirculation dump valve 58, and the recirculation dump duct 59 are provided to divert air-entrained fibers from the recirculation manifold 25 when apparatus 20 is turned off to prevent fibers in the recirculation manifold from precipitating deliterious ramifications during start-ups of apparatus 20.

EXEMPLARY EMBODIMENT OF APPARATUS 20

An exemplary apparatus of the configuration shown in FIG. 1 was sized and configured to make twelve articles 51 per revolution of the drum. In this apparatus, the articles are formed in deposition cavities having lengths of six-and-six-tenths inches (about 17.8 cm.) and which cavities are spaced eight-and-one-half inches (about 21.6 cm.) center-to-center about the periphery of the drum. The cavities are configured to be seven-tenths of an inch deep (about 1.8 cm) in their end regions, and one-and-three-tenths inches deep (about 3.3 cm) in their center spans in order to make articles 51 having nominal fiber weights of about eight grams each. The hood wraps the drum approximately one-hundred-eighty degrees, centered about the upstream wall of the discharge chute 23 as indicated in FIG. 1. The vacuum manifold 44 spans about two-hundred-sixty degrees of the drum, and is so disposed that its upstream end 52 is subjacent the upstream end of the hood and its downstream end 53 is positioned just upstream of the return roll 39 and nozzle 36. The lugged cylinder 34 is configured generally as shown with four lugs 35. The lugs are disposed on the same pitch as the pitch of the deposition cavities on drum 26 so that cylinder 34 and the drum mesh in a gear-like manner as they are rotated in synchronus relation. The disk hammermill 22 was obtained from Curt G. Joa, Inc., and is their hammermill model number 85R-9505-B. This hammermill acts somewhat like a quasi centrifugal air blower inasmuch as it draws air into its intake. Thus, by connecting the recirculation manifold 25 to the intake of the hammermill, no other means need be provided to effect flow in the recirculation manifold.

Apparatus 20 is preferably operated with the stream 50 having a length L of up to about fourteen inches (about 35.6 cm.), and more preferably from about ten to about twelve inches (about 25.4 to about 30.5 cm.); a velocity of stream 50 of from about two-thousand to about fifteen-thousand feet per minute (about 0.61 to about 4.57 Km. per minute), and more preferably from about six-thousand to about ten-thousand feet per minute (about 1.83 to about 3.05 Km. per minute); a flow rate of stream 50 of from about one-thousand to about fifteen-hundred cubic feet per minute (about 28.3 to about 42.5 cubic meters per minute); a fiber to air weight ratio in stream 50 of from about six-to-one to about thirty-to-one, and more preferably from about seven-to-one to about sixteen-to-one; and a peripheral velocity of drum 26 preferably from about two-hundred-fifty to about seven-hundred feet per minute (about 76.2 to about 213 meters per minute).

The drylap used in the exemplary apparatus described above was obtained from The Buckeye Cellulose Corporation and comprised from about seventy-five to about one-hundred percent native softwood fibers and from about zero to about twenty-five percent hardwood fibers.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. In an improved apparatus for making discrete airlaid articles which apparatus includes a foraminous deposition member, means for directing air-entrained fibers towards said foraminous deposition member, said deposition member being configured to have an endless series of discrete article formation cavities presented to said stream of air-entrained fibers, and means for vacuum exhausting the entrainment air from the apparatus, the improvement wherein said means for directing said air-entrained fibers comprises means for directing a spatially stationary, substantially columnar stream of air having discrete fibers entrained therein substantially perpendicular towards only a predetermined first span of said deposition member, and wherein said means for vacuum exhausting said entrainment air comprises means for the bulk of said entrainment air to be vacuum exhausted from said apparatus by being drawn through a second span of said deposition member disposed upstream from said columnar stream of air and said first span, and for the remainder of the entrainment air to be drawn through said first span.

2. The improved apparatus of claim 1 wherein said deposition member is configured to be a drum having said discrete formation cavities disposed in circumferentially spaced relation about its periphery; and said apparatus further comprises means for overfilling said cavities, and for scarfing and recycling the excess matter fibers.

3. The improved apparatus of claim 2 further comprising means for compacting each article airlaid in said formation cavities prior to commencing removing said articles from said formation cavities.

4. In an improved drum-type airlaying apparatus for making discrete absorbent fibrous articles which apparatus includes a rotating deposition drum having a plurality of radially outwardly facing article formation cavities disposed in circumferentially spaced relation about the periphery of the deposition drum and wherein each of the cavities has a foraminous bottom wall, means for directing air-entrained fibers towards the periphery of the drum, and means for vacuum drawing the entrainment air through the foraminous bottom walls of the cavities and exhausting it from the apparatus, the improvement wherein said means for directing air-entrained fibers comprises means for directing a substantially columnar stream of air having fibers entrained therein along an air-flow-direction that is oriented substantially radially inwardly towards only a predetermined first sector of the periphery of the drum, and wherein said means for vacuum drawing said entrainment air comprises means for the bulk of said entrainment air to be vacuum drawn inwardly through the foraminous bottom wall of at least one substantially empty said cavity disposed in a predetermined second sector of the periphery of the drum disposed circumferentially upstream from said columnar stream of air and said first sector of the periphery of the drum.

5. The improved drum-type airlaying apparatus of claim 4 further comprising means for imparting a downstream velocity component to said columnar stream which is substantially equal to the circumferential velocity of the drum.

6. The improved drum-type airlaying apparatus of claim 4 further comprising means for maintaining a sub-ambient static air pressure superjacent the radially outwardly facing areas of said second sector of the periphery of the drum.

7. The improved drum-type airlaying apparatus of claim 4 further comprising means for controlling the velocity of said columnar stream at a controlled value in the range of from about two-thousand to about fifteen-thousand feet per minute.

8. The improved drum-type airlaying apparatus of claim 7 wherein said controlled value is from about six-thousand to about ten-thousand feet per minute.

9. The improved drum-type airlaying apparatus of claim 4 further comprising means for controlling the air to fiber weight ratio to a controlled value in the range of from about six-to-one to about thirty-to-one.

10. The improved drum-type airlaying apparatus of claim 9 wherein said controlled value is in the range of from about seven-to-one to about sixteen-to-one.

11. The improved drum-type airlaying apparatus of claim 4 further comprising means for adjusting the airflow-direction length of said columnar stream to a preferred value of up to about fourteen inches.

12. The improved drum-type airlaying apparatus of claim 11 wherein said range is from about ten to about twelve inches.

13. The improved drum-type airlaying apparatus of claim 4 further comprising means for establishing the rate of flow of said stream at a preferred value in the range of from about one-thousand to about fifteen-hundred cubic feet per minute.

14. The improved drum-type airlaying apparatus of claim 4 wherein said first sector has a preferred angular extent of about forty or less degrees of the drum, and said second sector has a preferred angular extent of from about thirty to about ninety degrees of the drum.

15. The improved drum-type airlaying apparatus of claim 14 wherein said angular extent of said first sector is more preferably about thirty degrees or less of the drum, and said angular extent of said second span is about sixty degrees.

16. The improved drum-type airlaying apparatus of claim 4 wherein said apparatus further comprises means for overfilling said cavities; and means for scarfing and recycling excess said fibers.

17. The improved drum-type airlaying apparatus of claim 4, further comprising mechanical means for compacting said articles a predetermined amount prior to commencing discharging each from its respective formation cavity.

18. The improved drum-type airlaying apparatus of claim 17 wherein said means for compacting comprises a lugged cylinder having at least one lug which is sized and configured to precipitate said compaction by being rotated in timed relation with the drum, and disposed so that said lug rolls partially into and out of each said cavity as said lugged cylinder and the drum are rotated in timed relation.

* * * * *